United States Patent [19]
Doyle et al.

[11] Patent Number: 5,752,942
[45] Date of Patent: May 19, 1998

[54] FIVE BEVELED POINT GEOMETRY FOR A HYPODERMIC NEEDLE

[75] Inventors: Judith L. Doyle, Upper Saddle River, N.J.; Steven L. Koziol, Columbus, Nebr.

[73] Assignee: Becton Dickinson and Company, Franklin Lakes, N.J.

[21] Appl. No.: 670,255

[22] Filed: Jun. 20, 1996

[51] Int. Cl.⁶ .................................................... A61M 5/32
[52] U.S. Cl. .................................................. 604/274
[58] Field of Search ................................ 604/272–274

[56] References Cited

U.S. PATENT DOCUMENTS

| | | |
|---|---|---|
| 2,409,979 | 10/1946 | Huber . |
| 2,560,162 | 7/1951 | Ferguson . |
| 3,071,135 | 1/1963 | Baldwin et al. . |
| 3,308,822 | 3/1967 | De Luca . |
| 5,536,259 | 7/1996 | Utterberg . |
| 5,575,780 | 11/1996 | Saito ........................... 604/272 |

FOREIGN PATENT DOCUMENTS 8902938  11/1989  Netherlands ................. 604/272

Primary Examiner—Michael Powell Buiz
Assistant Examiner—Deborah Blyveis
Attorney, Agent, or Firm—Allen W. Wark

[57] ABSTRACT

A hypodermic needle featuring a multi-beveled point geometry is disclosed. In one embodiment, the multi-beveled point features a primary bevel, a pair of tip bevels, and a pair of middle bevels each intermediate the primary bevel and a respective one of the tip bevels. The primary and middle bevels are provided at angles of inclination, measured between the central axis and a reference plane that are substantially identical. The tip bevels are formed at an angle of inclination respective to the central axis which is not equal to the angle of inclination at which the primary and middle bevels are formed. The resulting five-beveled point geometry contributes to a more continuous bevel face free of abrupt intercepts or transitions between the respective bevel faces, lessening the penetration force required to urge the needle point through skin, flesh, or other material.

7 Claims, 4 Drawing Sheets

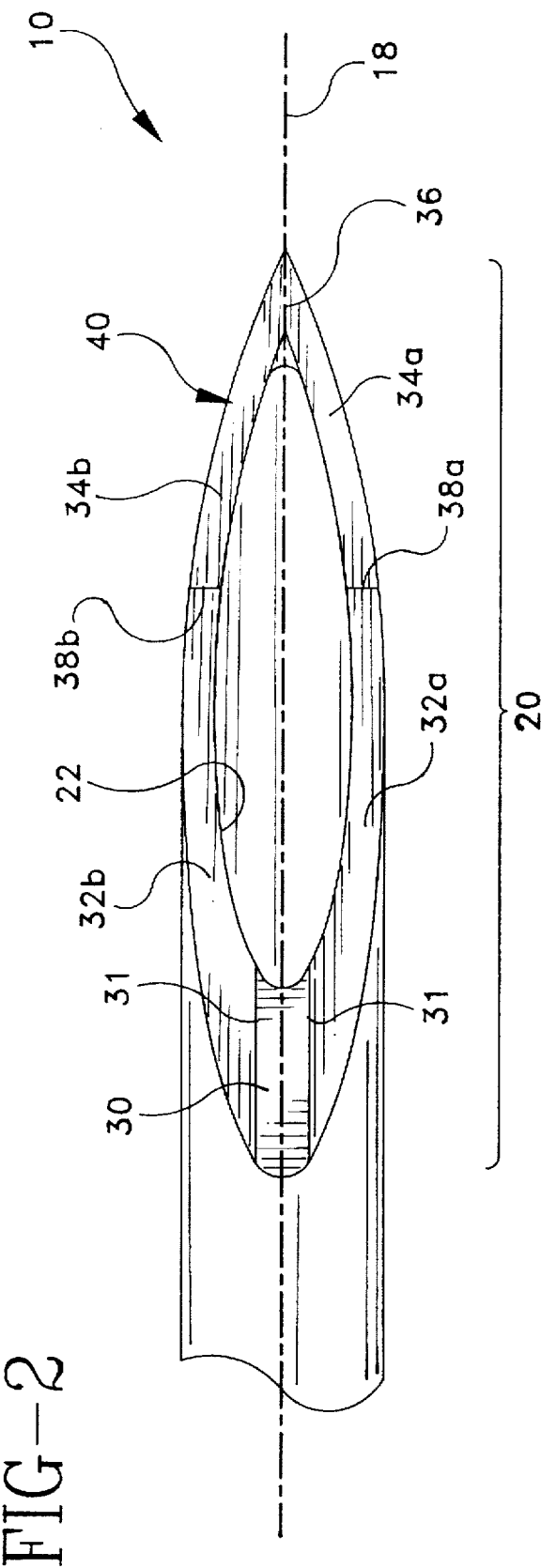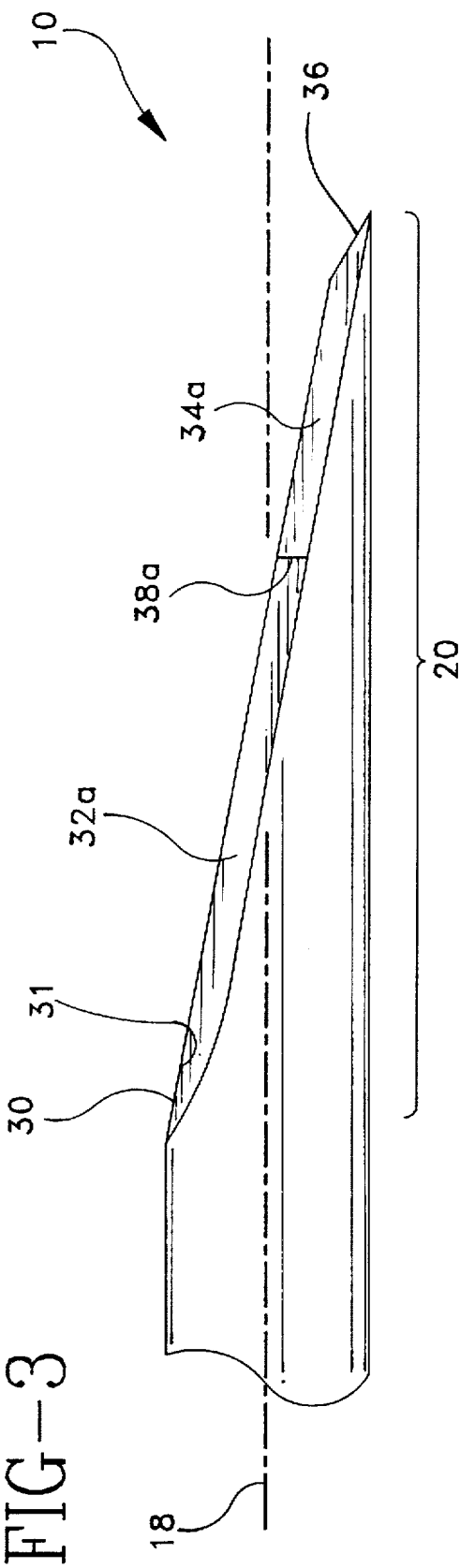

FIVE BEVELED POINT GEOMETRY FOR A HYPODERMIC NEEDLE

I. FIELD OF THE INVENTION.

The invention relates to a point geometry for a hypodermic needle, and more particularly, to a five beveled point geometry for a hypodermic needle for a reducing needle penetration force.

II. BACKGROUND.

A hypodermic needle is typically formed from an elongate tube or cannula having a fluid-conducting lumen and characterized by a central axis. The proximal end of the hypodermic needle is typically configured for mating to, or is otherwise affixed to, a fluid delivery device such as a hypodermic syringe. The distal end of the hypodermic needle is typically provided with a pointed tip geometry for piercing elastomeric septums and/or a patient's flesh or tissue so as to deliver the medicament held in the syringe. The practitioner may also employ the hypodermic needle for aspirating fluids held in a vessel such as a vial. This use often entails a practitioner inserting the pointed tip of the needle through a rubber or elastomeric-type seal associated with the vessel so that the practitioner can access the fluid contained within the vessel.

Various considerations merit address when designing the pointed tip of the hypodermic needle. For instance, one would like to minimize the needle penetration force necessary for urging the pointed tip of the needle through the skin and flesh structure of the patient. It is generally recognized that by reducing needle penetration force, the patient will experience less pain, making the injection more comfortable. Another consideration in designing point geometry is to prevent or otherwise minimize "coring". Coring, as the skilled artisan will appreciate, results when a portion of a material through which the needle has penetrated becomes lodged in the lumen adjacent the pointed tip.

Certain efforts in the art have sought to address one or more of the aforementioned concerns. One approach is found in U.S. Pat. No. 3,071,135 (Baldwin et al.). Here, the needle face is characterized by a pair of side facets (or "bevels"), which intersect with a main facet. The heel portion of the needle face includes an external recess which merges with a smoothly rounded surface or edge portion of the lumen opening. It is stated in this patent that the provision of the needle recess relieves tension of a membrane flap created upon entry of the needle, thereby reducing the penetration force. U.S. Pat. No. 2,560,162 (Ferguson) provides a similar structure, albeit with the provision of an additional pair of forward side bevels. An emphasis of this patent is that the provision of the recess (here referred to as a depression) prevents or minimizes the severing of a plug from a layer or layers being pierced by the needle. U.S. Pat. No. 3,308,822 (DeLuca) has as its objective minimizing the penetration force of a needle so as to minimize pain incident to an injection. This patent states to create, from an initial piercing point of the flesh, three substantially straight lines in the form of the letter "Y". It is stated that by forming the "Y" shaped cut, three substantially V-shaped flaps are formed, the three angular edges of which are capable of extension into a circular form in the opening of the skin, thereby preventing extensive stretching or tensioning of the edges of the cut. The needle point employs five faces produced by a series of five grinds, with the last two grinds resulting in bevels disposed not adjacent the opening of the needle, but rather on the back of the needle away from the opening. U.S. Pat. No. 2,409,979 (Huber) relates to a hypodermic needle also intended to reduce pain as the needle penetrates the tissue. Huber appears to describe a primary bevel mating with a pair of beveled surfaces that meet at a curved surface of diminishing area adjacent the end portion of the needle.

Despite the attempts in the art to arrive at a needle point geometry to lessen needle penetration forces, there continues to exist a need for a needle point geometry which displays reduced needle penetration forces and, hence, reduces the pain or discomfort level experienced by a patient. Such a needle point geometry is disclosed herein.

III. SUMMARY OF THE INVENTION.

It has been surmised by the inventors herein that a primary reason that a patient experiences pain when the needle is inserted is that a portion of the needle point "catches" on the skin or flesh as the needle penetrates. It has been reasoned by the inventors herein that one cause of a needle point catching the skin or flesh is due to the height of the "intercept" established at the transition between differing bevels forming the needle point. It is reasoned that if the transitions between differing bevels forming the needle point were less pronounced, the height of the intercepts would be reduced. The effect of reducing the heights of the transitions would be to approximate, from a series of bevels forming the point, a more continuous, unitary bevel face. The resulting continuous bevel point would require less penetration force to enter a patient's flesh. By reducing penetration forces, it is believed that the patient may experience less pain.

Accordingly, the invention relates to a multi-beveled needle point reducing the heights of the intercepts created between merging bevels that results in a more continuous bevel face. The needle includes a cannula having a lumen and a central axis therethrough. The multi-beveled needle point defines an opening to the lumen for the passage of fluids between a medical delivery device and a patient or vessel. The multi-beveled needle point preferably includes a primary bevel, a pair of tip bevels and a pair of middle bevels. Each of the middle bevels are contiguous with the primary bevel and meet a respective one of the tip bevels at an intersect. The primary bevel is formed or otherwise provided on the cannula by inclining the central axis of the needle cannula to a first planar angle respective of a reference plane.

Preferably, each of the middle bevels and tip bevels is formed by rotating the cannula along the central axis within a range of rotational angles respective to the position of the primary bevel. Preferably, the middle bevels are formed on the cannula at a planar angle substantially equal to if not identical to the first planar angle at which the primary bevel is formed. Preferably, each of the tip bevels is formed at a planar angle which is not equal to the first planar angle at which the primary bevel is formed. The resulting needle point, formed of five distinct bevels, displays reduced height intercepts, resulting in a more continuous bevel face about the opening. It is also surmised that by providing a series of five distinct bevels, the needle point is lengthened over needle points conventionally in use, and owing to the reduced height intervals, results in an effective outer diameter at the needle point less than the outer diameter of needle points currently in use, all of which contribute to reduced needle penetration forces.

IV. BRIEF DESCRIPTION OF THE DRAWINGS.

The invention will now be described in more detail by way of with reference to the appended drawings, wherein:

FIG. 2 is a top view of the multi-beveled needle tip of FIG. 1;

FIG. 3 is a side view of the multi-beveled needle tip of FIG. 1;

Figure 5:
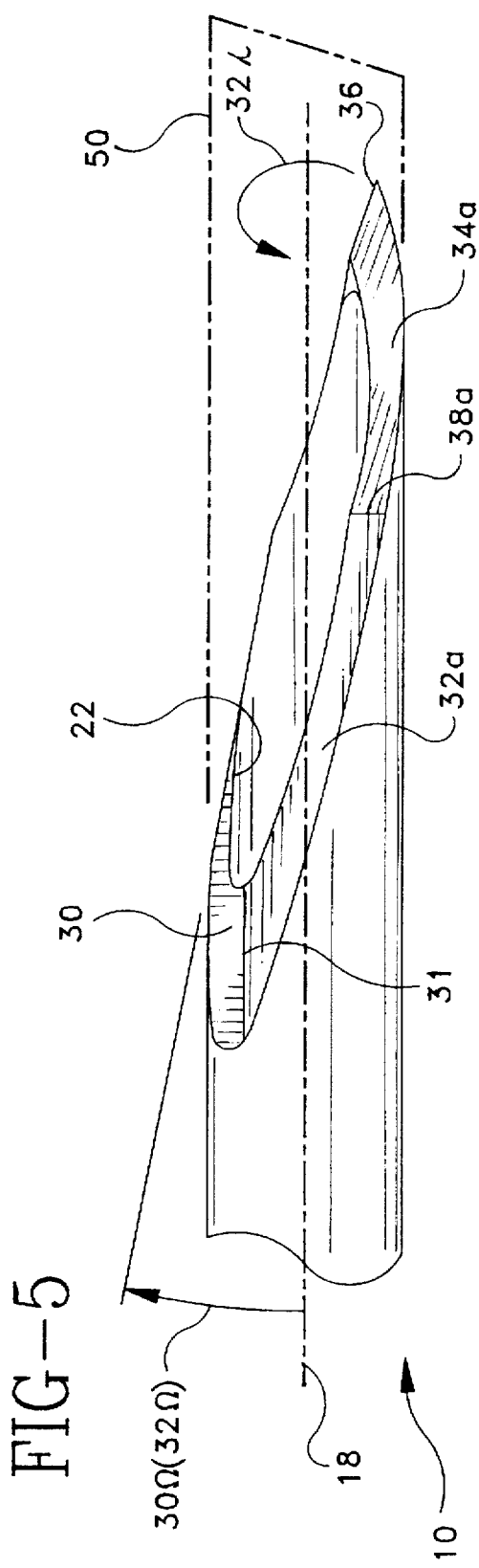
Figure 6:
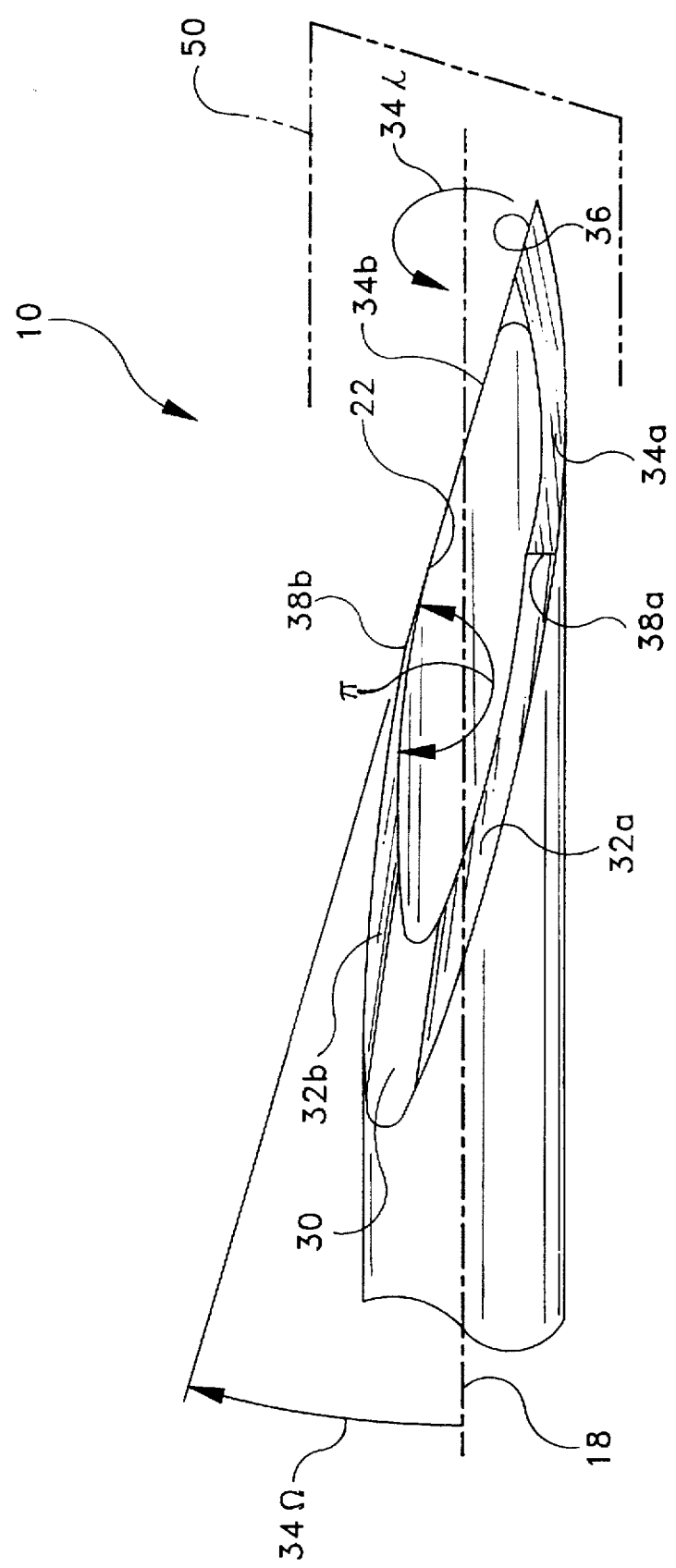

FIG. 5 is a second side view of a multi-beveled needle tip in accordance with the present invention, depicting the cannula rotated about the central axis at a first rotational angle and inclined at a first planar angle with respect to an imaginary plane extending through the central axis for forming the middle bevels; and FIG. 6 is a third side view of a multi-beveled needle tip in accordance with the present invention, depicting the cannula rotated at a second rotational angle about the central axis of the cannula and inclined at a second planar angle with respect to an imaginary plane extending through the central axis for forming the tip bevels.

V. DETAILED DESCRIPTION OF THE DRAWINGS.

A convention employed in this application is that the term "proximal" denotes a direction closest to a practitioner, while the term "distal" denotes a direction furthest from a practitioner.

Turning now to the drawings, wherein like numeral denote like components, FIGS. 1-6 depict a hypodermic needle 10 characterized by a multi-beveled point 20 in accordance with the present invention. As the skilled artisan will appreciate, hypodermic needle 10 can be formed from a tube or cannula 11 defining therein a fluid carrying duct or lumen 16. Hypodermic needle 10 includes a proximal end 14 which can be attached in fluid communication with a medical delivery instrument (not shown). Multi-beveled point 20 defines a fluid opening 22 for passage of fluids to and from fluid carrying lumen 16. The fluid carrying lumen is characterized by a central axis 18.

Multi-beveled point 20 is characterized by a length "L" and is formed through a plurality of individual bevels that together define a beveled face 40 about the periphery of fluid opening 22. In the embodiment disclosed by applicants herein, the multi-beveled point is characterized by a primary bevel 30; a pair of middle bevels 32a, 32b; and a pair of tip bevels 34a, 34b. Each of the pair of middle bevels 32a, 32b and each of the pair of tip bevels 34a, 34b are substantially symmetrically formed on opposite sides of primary bevel 30, as will be further described hereinbelow. Adjacent middle and tip bevels 32a, 34a meet at an intersect 38a demarcating the respective planes at which the middle and tip bevels are formed. Adjacent middle and tip bevels 32b, 34b likewise meet at an intersect 38b. Tip bevels 34a, 34b meet at appointed apex 36 which first enters the skin of a patient (or sealing material associated with a fluid carrying vessel).

Figure 1:
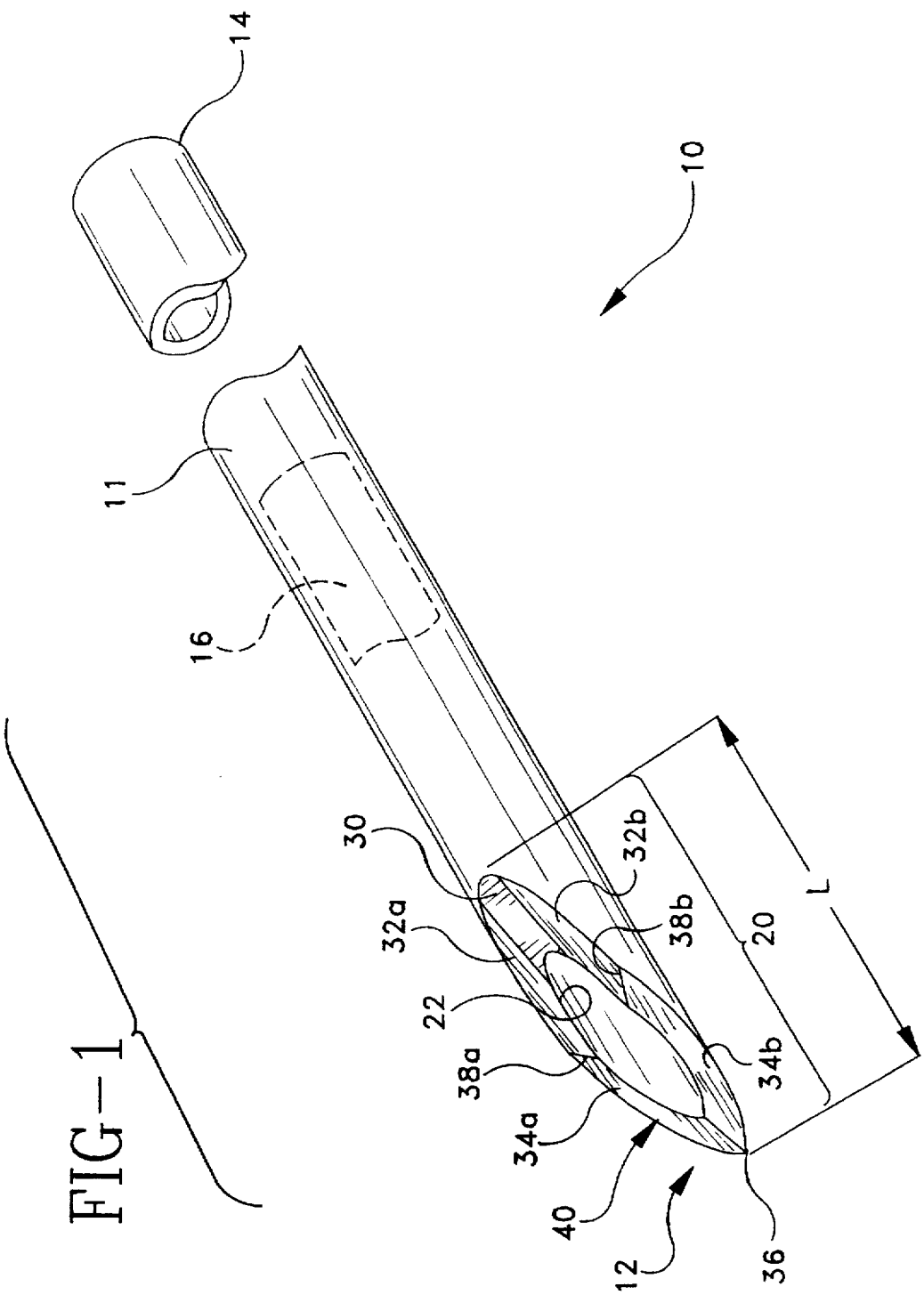
FIG. 1 is a frontal perspective view of a multi-beveled needle tip geometry in accordance with the present invention.
Figure 4:
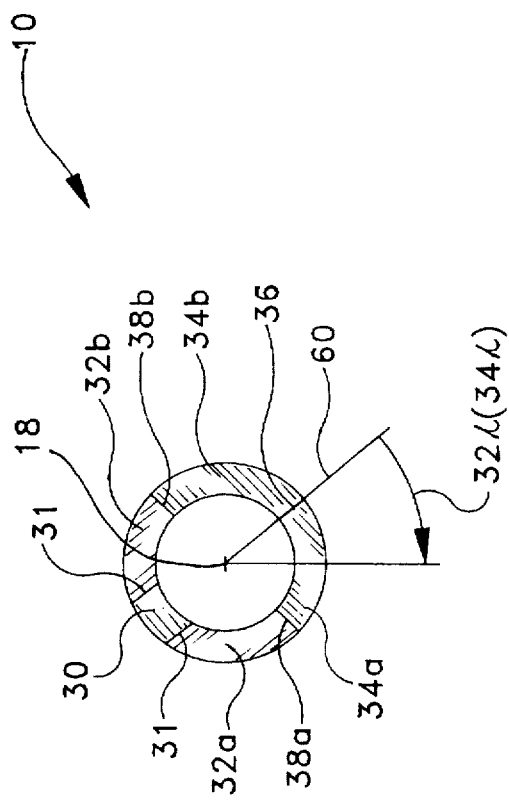
FIG. 4 is a frontal view of the multi-beveled needle tip of FIG. 1, depicting rotational angles about the central axis of the cannula for forming the middle bevels and tip bevels.

Primary bevel 30, middle bevels 32a, 32b and tip bevels 34a, 34b are formed or otherwise provided on cannula 10 by inclining and/or rotating cannula 10 through a series of angles measured relative to central axis 18. In the embodiment depicted herein, and as best illustrated in FIGS. 4, 5 and 6, primary bevel 30 is formed or otherwise provided on hypodermic needle 10 by inclining central axis 18 of hypodermic needle at an angle 30Ω measured relative to a reference plane 50. The reference plane 50 can represent, for instance, a grinding wheel which, as the skilled artisan will appreciate, is one way to form bevels on a hypodermic needle. For purposes of explaining the formation of the middle bevels and the tip bevels, the location of primary bevel 30 on the hypodermic needle can be established by a midline rotational position 60 (see FIG. 4) about central axis 18.

Middle bevels 32a, 32b and tip bevels 34a, 34b can likewise be formed or otherwise provided on hypodermic needle 10 by inclining the central axis of hypodermic needle 10 at some angle relative to reference plane 50, as well as by rotating hypodermic needle 10 about the central axis at some angle relative to mid-line rotational position 60 of primary bevel 30. In the embodiment depicted herein, each of middle bevels 32a, 32b are formed or otherwise provided on hypodermic needle 10 by inclining central axis 18 of the hypodermic needle at an angle 32Ω relative to the reference plane 50, and by rotating the hypodermic needle about central axis 18 at a rotational angle 32λ. Similarly, tip bevels 34a, 34b are formed or otherwise provided on hypodermic needle 10 by inclining the central axis 18 of hypodermic needle 10 at an angle 34Ω relative to reference plane 50, and by rotating the hypodermic needle about central axis 18 at a rotational angle 34λ. For purposes of simplicity, FIGS. 4, 5 and 6 depict inclination and/or rotation of hypodermic needle 10 so as to form, when viewing the hypodermic needle from the frontal position of FIG. 4, left side middle bevel 32a and left side tip bevel 34a. However, it will be evident to the skilled artisan that formation of right-side middle bevel 32b and right-side tip bevel 34b is effected by reversing the rotation of needle 10 about central axis 18.

It has been surmised by the applicants herein that optimum results for reducing the height of intercepts 38a, 38b is achieved by forming primary bevel 30 and each of middle bevels 32a, 32b at angles of inclination 30Ω and 32Ω which are substantially equal if not identical. For instance, it has been found by applicants herein that optimum results are achieved by setting both inclination angles 30Ω and 32Ω, respective to imaginary plane 50, in a range of about 9 degrees ("°") plus or minus 1°. For purposes of simplicity, the transition demarcating primary bevel 30 from each of middle bevels 32a, 32b has been denoted by the numeral 31. It is surmised that by not varying the angle of inclination 32Ω for the middle bevels from angle of inclination 30Ω for the primary bevel, transition 31 demarcating primary bevel 30 from middle bevels 32a, 32b will be more rounded and less pronounced, contributing to a smoother, more continuous bevel face 40. Subsequent to formation of primary bevel 30, the hypodermic needle is rotated about the central axis 18 in both the clockwise and counterclockwise directions at rotational angle 32λ to form middle bevels 32a, 32b. It has been found by the applicants herein that optimum results are obtained when the range of rotational angle 32λ is about 23° plus or minus 5°.

Tip bevels 34a, 34b are likewise formed or otherwise provided on hypodermic needle 10 by inclining central axis 18 of hypodermic needle 10 to an angle 34Ω relative to reference plane 50, and by rotating the hypodermic needle about central axis 18 to an angle 34λ. It has been found by the applicants herein that optimum results for reducing the height of intercepts 38a, 38b demarcating the respective middle and tip bevels results when needle cannula 10 is inclined at an angle 34Ω in a range of about 15° plus or minus 2°, and when the needle cannula is rotated to an angle 34Ω in a range measuring about 23° plus or minus 5°.

FIG. 3 exemplifies the side profile of multi-beveled needle tip 20 formed in accordance with the present invention. Intercept 38a is reduced in height to an extent that when viewed from the side, middle bevel 32a and tip bevel 34a appear to provide a substantially-straight profile. The same effect can be seen in FIG. 6, where middle and tip bevels 32b, 34b, when viewed in side profile, define an angle "π" that is nearly 180° as measured about intercept 38b. The effect is a more continuous bevel face 40 free of abrupt intercepts 38a, 38b (or for that matter, transitions 31 demarcating the primary middle bevels), resulting in a needle tip requiring less penetration force. By reducing the heights of intercepts 38a, 38b, the effective outer diameter of needle point 20 is reduced, helping to reduce needle penetration forces.

The hypodermic needle 10 in accordance with the present invention can be formed from conventional materials such as steel. It will be realized by the skilled artisan that medical grade plastics, composites, ceramics, or like materials can be substituted. The needle can be lubricated with various conventional lubricants such as silicone oils to enhance the effects obtained by applicant's geometry. The bevels can be formed on the hypodermic needle by conventional processes such as by grinding.

It will be evident to the skilled artisan that the bevels can be formed in any order desired. In one iteration, the primary and middle bevels can be formed before the tip bevels, in that in the preferred embodiment, the primary and middle bevels are formed at substantially identical angles of inclination 30Ω, 32Ω, and this might contribute to greater manufacturing efficiency. However, other manufacturing iterations can be employed. For instance, the tip bevels can be formed prior to manufacturing either of the middle or primary bevels. A further iteration would be to form the middle bevels 32a, 32b intermediate the steps required for forming primary bevel 30 and tip bevels 34a, 34b. For instance, the central axis of the hypodermic needle can be first inclined to angle 30Ω for formation of the primary bevel. Thereafter, the central axis of the hypodermic needle can be inclined to angle 34Ω, and thereafter rotated about central axis 18 to angles of rotation 34λ, for formation of the tip bevels. Thereafter, central axis of hypodermic needle 10 can be re-inclined to angle 32Ω, and rotated about central axis 18 to angles 32λ, for formation of the middle bevels. It will be realized by the skilled artisan that any order for forming the respective bevels for needle tip 20 that results in continuous bevel face 40 will achieve the advantages and results of the invention herein.

One particular sequence performed by the inventors herein has resulted in the formation of consistently good needle points 20. Needle point 20 was produced on a 27 gauge needle by grinding. Central axis 18 of hypodermic needle 10 was inclined at an angle of about 14.5 degrees respective of the grinding wheel for an initial "hog-off" grind. Thereafter, central axis 18 of the hypodermic needle was subjected to a series of angles of inclination and rotation in order to form a pair of adjacent middle and tip bevels prior to formation of an opposed pair of adjacent and middle tip bevels, with the primary bevel formed as a last grind. In the iteration performed by the inventors herein, subsequent to the hog-off grind, central axis 18 of the hypodermic needle was inclined with angle 32Ω of about 9 degrees, and thereafter rotated right around central axis 18 to an angle 32λ of about 20 degrees. At this point, left-side middle bevel 32a was ground. Thereafter, maintaining the rotational position 32λ of the central axis, central axis 18 was inclined to an angle 34Ω of about 14.5 degrees and left-side tip bevel 34a was ground (note that angle of rotation 34λ is the same 20 degree angle established for angle of rotation 32λ). After the left side middle and tip bevels were ground, central axis 18 of the needle cannula was repositioned to the angle of inclination 32Ω of about 9 degrees, and rotated 40 degrees to the left of the position where the left side middle and tip bevels had been ground. At this point, right middle bevel 32b was ground. Thereafter, maintaining central axis 18 of the needle in its rotational position, the central axis was inclined to an angle of inclination 34Ω of about 14.5 degrees and tip bevel 34b was ground. Thereafter, central axis 18 of the needle cannula was rotated 20 degrees back to its center position, the central axis 18 positioned at an angle of inclination 30Ω of about 9 degrees, and primary bevel 30 was ground.

Tests were conducted comparing penetration force in rubber vial stoppers (20 millimeter rubber vial stoppers, model number 88-29530, manufactured by Abbott Laboratories of Ashland, Ohio) of 26 gauge needles produced in accordance with the above-identified steps against penetration forces exhibited by existing 26 gauge needles currently employed in HYPAK®-brand prefillable syringes, manufactured by Becton Dickinson Pharmaceutical Systems of Le Pont de Claix, France. Each of the needles were lubed with polydimethylsiloxane. Various angles of rotation 32λ, 34λ and angles of inclination 30Ω, 32Ω and 34Ω were tested. The resulting table illustrates that 26 gauge needles displaying needle point 20 according to the invention had significantly reduced needle penetration forces as compared to existing product:

TABLE I 26G 5-Bevel Needles
All needles lubed with polydimethylsiloxane
Rubber Vial Penetration Forces in Gram Force
(Average HYPAK Brand Needle Control Force = 468.5 gmf)

| Angle of Rotation | | Angle Of Inclination | | | |
|---|---|---|---|---|---|
| 32λ | 34λ | 30Ω, 32Ω | 34Ω | Point Length ("L").094 Tip Bevel Length .036" | Point Length .080" Tip Bevel Length .040" |
| 35° | 35° | 10° | 10° | 341.5 gm.f | |
| 30° | 30° | 10° | 10° | 338.1 gm.f | |
| 22° | 22° | 10° | 16° | 344.5 gm.f | |
| 22° | 22° | 13° | 16° | | 359.0 gm.f |

The formation of a multi-beveled tip as described herein results in a bevel face 40 which is more continuous, free of abrupt intercepts or transitions. Absent abrupt intercepts or transitions, the likelihood that a portion of the bevel face will catch the skin or flesh of a patient is reduced, and the effective outside diameter of the needle point will be reduced, all meaning that needle penetration forces will be lessened.

It will be appreciated and understood by those skilled in the art that further and additional forms of the invention may be devised without departing from the spirit and scope of the appended claims, the invention not being limited to the specific embodiments shown.

We claim:

1. A needle having a multi-beveled point, comprising:

a cannula having a lumen and a central axis therethrough, said multi-beveled point provided at one end of the cannula, said multi-beveled point comprised of a primary bevel, a pair of tip bevels, and a pair of middle bevels, each of said pair of middle bevels intermediate said primary bevel and one of said pair of tip bevels, wherein each of said pair of tip bevels meets a respective middle bevel at an intersection line, wherein respective of angles defined between said central axis and a reference plane, said primary bevel is provided on said cannula at a first planar angle, said pair of middle bevels are provided on said cannula at a second planar angle, and said pair of tip bevels are provided on said cannula at a third planar angle, and wherein respective of an angle of rotation about said central axis, said primary bevel is provided at a first rotational angle, said pair of middle bevels are each provided at a second rotational angle, and said pair of tip bevels are each provided at a third rotational angle, wherein said first and second planar angles are substantially equal.

2. The needle of claim 1, wherein said first and second planar angles are in the range of 9 degrees plus or minus 1 degree.

3. The needle of claim 1, wherein said third planar angle is in the range of 15 degrees plus or minus 2 degrees.

4. The needle of claim 1, wherein said second rotational angle is in the range of 18.5 degrees plus or minus 5 degrees.

5. The needle of claim 1, wherein said third rotational angle is in the range of 23 degrees plus or minus 5 degrees.

6. The needle of claim 1 wherein said second and third rotational angles are 22 degrees.

7. The needle of claim 1, wherein said cannula is formed from a metallic material.

* * * * *